(12) United States Patent
Kobayashi et al.

(10) Patent No.: US 12,351,692 B2
(45) Date of Patent: Jul. 8, 2025

(54) ABSORBENT RESIN PARTICLES AND ABSORBENT

(71) Applicant: SUMITOMO SEIKA CHEMICALS CO., LTD., Hyogo (JP)

(72) Inventors: Tetsuhiro Kobayashi, Himeji (JP); Hiroki Sawaki, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 237 days.

(21) Appl. No.: 17/757,136

(22) PCT Filed: Dec. 9, 2020

(86) PCT No.: PCT/JP2020/045921
§ 371 (c)(1),
(2) Date: Jun. 9, 2022

(87) PCT Pub. No.: WO2021/117780
PCT Pub. Date: Jun. 17, 2021

(65) Prior Publication Data
US 2023/0036813 A1    Feb. 2, 2023

(30) Foreign Application Priority Data

Dec. 13, 2019 (JP) .................. 2019-225184
Dec. 13, 2019 (JP) .................. 2019-225185
(Continued)

(51) Int. Cl.
*C08L 101/14* (2006.01)
*B01J 20/24* (2006.01)
(Continued)

(52) U.S. Cl.
CPC ............... *C08J 3/126* (2013.01); *B01J 20/24* (2013.01); *B01J 20/26* (2013.01); *B01J 20/261* (2013.01);
(Continued)

(58) Field of Classification Search
CPC ............ C08J 3/075; C08J 3/126; C08J 3/245
See application file for complete search history.

(56) References Cited

U.S. PATENT DOCUMENTS 5,248,709 A    9/1993  Brehm
2009/0105389 A1*  4/2009  Walden .................. C08L 101/14
                                                          524/437
(Continued)

FOREIGN PATENT DOCUMENTS

EP    0703265 B1   9/2001
EP    1882701 A1   1/2008
(Continued)

OTHER PUBLICATIONS

Machine translation JP-2011178969-A (Year: 2024).*
(Continued)

*Primary Examiner* — Alexandre F Ferre
(74) *Attorney, Agent, or Firm* — HSML P.C.

(57) ABSTRACT

The present disclosure relates to water-absorbent resin particles in which a contact angle of 0.9% by mass saline at 25° C.±2° C. is 100 degrees or larger, and an absorbent material containing the water-absorbent resin particles.

16 Claims, 2 Drawing Sheets

(30) Foreign Application Priority Data

| Feb. 19, 2020 | (JP) | 2020-026078 |
| May 14, 2020 | (JP) | 2020-085218 |
| May 14, 2020 | (JP) | 2020-085220 |
| May 14, 2020 | (JP) | 2020-085224 |
| May 14, 2020 | (JP) | 2020-085226 |
| May 14, 2020 | (JP) | 2020-085227 |
| Jul. 17, 2020 | (JP) | 2020-122800 |

(51) Int. Cl.
- *B01J 20/26* (2006.01)
- *B01J 20/28* (2006.01)
- *C08F 2/08* (2006.01)
- *C08F 20/06* (2006.01)
- *C08F 120/06* (2006.01)
- *C08G 65/08* (2006.01)
- *C08J 3/12* (2006.01)
- *C08J 3/16* (2006.01)
- *C08L 33/26* (2006.01)

(52) U.S. Cl.
CPC ............ *B01J 20/262* (2013.01); *B01J 20/264* (2013.01); *B01J 20/265* (2013.01); *B01J 20/28* (2013.01); *B01J 20/28016* (2013.01); *C08F 2/08* (2013.01); *C08F 20/06* (2013.01); *C08F 120/06* (2013.01); *C08G 65/08* (2013.01); *C08J 3/16* (2013.01); *C08L 33/26* (2013.01); *C08L 101/14* (2013.01)

(56) References Cited

U.S. PATENT DOCUMENTS

| 2015/0368409 A1* | 12/2015 | Pakusch | C04B 24/2641 |
| | | | 525/218 |
| 2018/0079847 A1* | 3/2018 | Lee | C08J 3/24 |

FOREIGN PATENT DOCUMENTS

| JP | H7-309971 | 11/1995 |
| JP | 2579814 B2 | 2/1997 |
| JP | H11-347402 | 12/1999 |
| JP | 2002-212301 | 7/2002 |
| JP | 2003-301019 | 10/2003 |
| JP | 2005-097569 A | 4/2005 |
| JP | 2006-199805 | 8/2006 |
| JP | 2007-506532 | 3/2007 |
| JP | 2008-538121 | 10/2008 |
| JP | 2009-035657 | 2/2009 |
| JP | 2010-241975 | 10/2010 |
| JP | 2011-178969 | 9/2011 |
| JP | 2013-213083 | 10/2013 |
| JP | 2014-098172 | 5/2014 |
| JP | 5485805 B2 | 5/2014 |
| JP | 2016-028117 | 2/2016 |
| JP | 2016-540107 | 12/2016 |
| JP | 2019-518839 | 7/2019 |
| WO | 99/037395 | 7/1999 |
| WO | 2005/030278 | 4/2005 |
| WO | 2006/082239 | 8/2006 |
| WO | 2015/084060 | 6/2015 |
| WO | 2018/147600 | 8/2018 |
| WO | 2020/122214 | 6/2020 |

OTHER PUBLICATIONS

Law, J. Phys Chem. Lett. 2014, 5, 686-688 (Year: 2014).*

International Search Report of PCT/JP2020/045921, Mar. 9, 2021, 3 pages.

International Preliminary Report on Patentability of PCT/JP2020/045921, Jun. 23, 2022, 5 pages.

* cited by examiner

ABSORBENT RESIN PARTICLES AND ABSORBENT

TECHNICAL FIELD

The present invention relates to water-absorbent resin particles and an absorbent material.

BACKGROUND ART

Water-absorbent resin particles are widely used in various fields of sanitary materials such as paper diapers, hygiene products, and portable toilets; agricultural and horticultural materials such as water retention agents and soil improvement agents; and industrial materials such as waterproofing agents and condensation prevention agents. An absorbent material containing water-absorbent resin particles has been used in an absorbent article for absorbing a liquid (for example, urine) having water as a main component (refer to Patent Literature 1 and Patent Literature 2, for example).

CITATION LIST

Patent Literature

[Patent Literature 1] JP 2006-199805 A
[Patent Literature 2] JP 2016-28117 A

SUMMARY OF INVENTION

Technical Problem

The water-absorbent resin particles in the absorbent material are required to have excellent liquid diffusibility in addition to a high water absorption amount. The inventors of the present invention have found that, in an absorbent material containing water-absorbent resin particles having a high liquid permeability, liquid diffusibility is excellent, but the amount of re-wet of the absorbed liquid tends to increases.

An object of the present invention is to provide water-absorbent resin particles capable of achieving both excellent liquid diffusibility and a practically sufficient amount of re-wet when used as an absorbent material.

Solution to Problem

One aspect of the present invention relates to water-absorbent resin particles in which a contact angle of 0.9% by mass saline at 25° C. 2° C. is 100 degrees or larger.

Another aspect of the present invention relates to an absorbent material containing the above-mentioned water-absorbent resin particles.

Advantageous Effects of Invention

According to the present invention, water-absorbent resin particles which are capable of achieving both excellent liquid diffusibility and a practically sufficient amount of re-wet when used as an absorbent material can be provided.

DESCRIPTION OF EMBODIMENTS

Hereinafter, some embodiments of the present invention will be described in detail. However, the present invention is not limited to the following embodiments.

In the present specification, "acrylic" and "methacrylic" are collectively referred to as "(meth)acrylic". "Acrylate" and "methacrylate" are also referred to as "(meth)acrylate". "(Poly)" means both of a case where there is a prefix of "poly" and a case where there is no prefix thereof. Regarding numerical value ranges described in a stepwise manner in the present specification, an upper limit value or a lower limit value of a numerical value range in a certain step can be arbitrarily combined with an upper limit value or a lower limit value of a numerical value range in another step. In a numerical value range described in the present specification, an upper limit value or a lower limit value of the numerical value range may be replaced with a value shown in examples. For materials exemplified in the present specification, one kind may be used alone, or two or more kinds may be used in combination. In a case where there are a plurality of substances corresponding to each of components in a composition, a content of each of the components in the composition means a total amount of the plurality of substances present in the composition unless otherwise specified. "Physiological saline" refers to an aqueous solution of 0.9% by mass sodium chloride. "Room temperature" refers to 25° C.±2° C. The term "layer" includes not only a structure having a shape formed on the entire surface when observed as a planar view, but also a structure having a shape partially formed.

[Water-Absorbent Resin Particles]

In water-absorbent resin particles of the present embodiment, a contact angle of 0.9% by mass saline at 25° C.±2° C. (physiological saline at room temperature) is 100 degrees or larger. By using the water-absorbent resin particles having a high contact angle for an absorbent material, water absorption is unlikely to be started because of repelling of water, but a liquid is easily diffused in the initial stage when the water-absorbent resin particles come into contact with the liquid. In addition, since water absorption is started in a state where the liquid is sufficiently diffused, it is presumed that an increase in the amount of re-wet can be prevented.

From the viewpoint of achieving both excellent liquid diffusibility and a practically sufficient amount of re-wet, the contact angle of the water-absorbent resin particles of the present embodiment is 100 degrees or larger. Furthermore, the contact angle of the water-absorbent resin particles may be 102 degrees or larger, 104 degrees or larger, or 108 degrees or larger, and may be 130 degrees or smaller, 128 degrees or smaller, 125 degrees or smaller, or 120 degrees or smaller. Furthermore, from the viewpoint of achieving both excellent liquid diffusibility and an excellent amount of re-wet, the contact angle of the water-absorbent resin particles may be 118 degrees or smaller, 115 degrees or smaller, or 114 degrees or smaller. In this case, the lower limit value of the contact angle may be the values listed above.

The contact angle is a value measured according to JIS R 3257 (1999) "Testing method of wettability of glass substrate". The contact angle in the present embodiment can be measured by a test performed in the order of i) and ii) below.

i) At 25° C.±2° C., a liquid droplet corresponding to 0.01 g of physiological saline is added dropwise onto the surface of the water-absorbent resin particles to bring the water-absorbent resin particles into contact with the liquid droplet.

ii) The contact angle of the liquid droplet is measured 0.1 seconds after when the liquid droplet comes into contact with the surface of the water-absorbent resin particles.

When the water absorption rate of the water-absorbent resin particles of the present embodiment is 55 seconds or more by a Vortex method, the effect by the present invention is more likely to be exhibited. The water absorption rate of the water-absorbent resin particles may be 56 seconds or more, 58 seconds or more, 60 seconds or more, or 61 seconds or more, and may be 180 seconds or less, 150 seconds or less, 120 seconds or less, 100 seconds or less, 95 seconds or less, or 92 seconds or less. The water absorption rate can be measured according to the Vortex method (Japanese Industrial Standard JIS K 7224 (1996)). Specifically, it is possible to obtain the water absorption rate as the time [second] from after the addition of the water-absorbent resin particles until the vortex disappears and the liquid surface becomes flat, when 2.0±0.002 g of the water-absorbent resin particles are added to 50±0.1 g of physiological saline stirred at 600 rpm (rpm=min$^{-1}$) in a 100 mL beaker with a flat bottom surface.

The water retention amount of physiological saline of the water-absorbent resin particles may be 32 g/g or more, 34 g/g or more, or 35 g/g or more, and may be 60 g/g or less, 55 g/g or less, 50 g/g or less, 45 g/g or less, or 43 g/g or less, for example. Furthermore, from the viewpoint of achieving both excellent liquid diffusibility and an excellent amount of re-wet, the water retention amount of physiological saline of the water-absorbent resin particles may be 37 g/g or more, 39 g/g or more, or 40 g/g or more. In this case, the upper limit value of the water retention amount may be the values listed above. The water retention amount of physiological saline is measured by a method described in Examples to be described later.

The constitution of the water-absorbent resin particles of the present embodiment is not particularly limited as long as the contact angle of physiological saline at room temperature is 100 degrees or larger. The contact angle can be adjusted by (1) adjusting the amount and/or HLB of a surfactant which may be used in a polymerization step of reverse phase suspension polymerization, (2) forming a coating layer that coats at least a part of the surface of a polymer particle having water absorption properties, or (3) adopting both (1) and (2) above, for example. Hereinafter, the method of (2) will be described.

The polymer particle is not particularly limited as long as it is composed of a resin having water absorption properties. The polymer particle may contain a crosslinking polymer formed by polymerizing a monomer containing an ethylenically unsaturated monomer, for example. The crosslinking polymer can have a monomer unit derived from the ethylenically unsaturated monomer. The polymer particles can be produced by a method including a step of polymerizing monomers including ethylenically unsaturated monomers, for example. Examples of methods of polymerization include a reverse phase suspension polymerization method, an aqueous solution polymerization method, a bulk polymerization method, and a precipitation polymerization method.

The ethylenically unsaturated monomer may be a water-soluble ethylenically unsaturated monomer (for example, an ethylenically unsaturated monomer having the solubility of 1 g or more in 100 g of water at 98° C.). Examples of the ethylenically unsaturated monomers include (meth)acrylic acid and a salt thereof, 2-(meth)acrylamide-2-methylpropanesulfonic acid and a salt thereof, (meth)acrylamide, N,N-dimethyl (meth)acrylamide, 2-hydroxyethyl (meth) acrylate, N-methylol (meth)acrylamide, polyethylene glycol mono(meth)acrylate, N,N-diethylaminoethyl (meth)acrylate, N,N-diethylaminopropyl (meth)acrylate, and diethylaminopropyl (meth)acrylamide. In a case where an ethylenically unsaturated monomer has an amino group, the amino group may be quaternized. The ethylenically unsaturated monomer may be used alone or in a combination of two or more kinds thereof.

From the viewpoint of industrial availability, the ethylenically unsaturated monomer may include at least one compound selected from the group consisting of (meth) acrylic acid and a salt thereof, acrylamide, methacrylamide, and N,N-dimethyl acrylamide. The ethylenically unsaturated monomer may include at least one compound selected from the group consisting of (meth)acrylic acid and a salt thereof, and acrylamide.

When the ethylenically unsaturated monomer has an acid group, the acid group may be neutralized and then used in the polymerization reaction. The degree of neutralization in the ethylenically unsaturated monomer may be 10 to 100 mol %, 50 to 90 mol %, or 60 to 80 mol % of the acid group in the ethylenically unsaturated monomer.

For the monomer for obtaining the polymer particles, a monomer other than the above-mentioned ethylenically unsaturated monomers may be used. Such a monomer can be used by, for example, being mixed with an aqueous solution containing the above-mentioned ethylenically unsaturated monomers. A use amount of the ethylenically unsaturated monomer may be 70 to 100 mol % with respect to a total amount of the monomers (the total amount of the monomers for obtaining the water-absorbent resin particles, for example, a total amount of monomers that gives a structural unit of a crosslinking polymer, the same shall apply hereinafter).

Crosslinking by self-crosslinking may occur during polymerization, but crosslinking of the polymer particles may be induced by using an internal crosslinking agent. When the internal crosslinking agent is used, water-absorbent characteristics (water retention amount and the like) of the water-absorbent resin particles are easily controlled. The internal crosslinking agent is usually added to a reaction solution during the polymerization reaction. Examples of the internal crosslinking agent include polyglycidyl compounds such as (poly)ethylene glycol diglycidyl ether, (poly)propylene glycol diglycidyl ether, (poly)glycerin diglycidyl ether, (poly)glycerin triglycidyl ether, (poly)propylene glycol polyglycidyl ether, and polyglycerol polyglycidyl ether.

The polymer particles may be particles in which crosslinking (surface crosslinking) is performed in the vicinity of the surface. The polymer particles may be constituted of only the crosslinking polymer particles, but may further contain a gel stabilizer, a metal chelating agent, a flowability improver (lubricant), and the like, for example. These components may be disposed inside the crosslinking polymer particles, or on the surface of the crosslinking polymer particles, or inside and on the surface thereof.

The shape of the polymer particle is not particularly limited, and may be substantially spherical, crushed, granular, or the like, and may be a shape in which primary particles having these shapes are aggregated, for example.

The median particle diameter of the polymer particles may be 130 to 800 μm, 200 to 850 μm, 250 to 700 μm, 300 to 600 μm, or 300 to 450 μm. The polymer particles may have a desired particle size distribution at the time of being obtained by a production method to be described later, but the particle size distribution may be adjusted by performing an operation such as particle size adjustment using classification with a sieve.

The coating layer preferably contains a water-insoluble component. In the present specification, the water-insoluble component may include not only a substance that is completely insoluble in water but also a substance that is slightly soluble in water (a substance that is sparingly soluble in water). The solubility of the water-insoluble component in 100 g of water is less than 10 g at 25° C., preferably less than 5 g, more preferably less than 3 g, and further preferably less than 1 g, for example.

From the viewpoint of easily adjusting the contact angle of the water-absorbent resin particles, for the water-insoluble component, it is preferable to use at least one selected from the group consisting of polyurethanes, polyolefins, polyesters, polyamides, polystyrenes, polycarbonates, polyacrylates, polyacetals, and acid-modified products thereof, it is more preferable to use at least one selected from the group consisting of polyolefins, polyurethanes, polyesters, and acid-modified products thereof, it is further preferable to use at least one selected from the group consisting of polyolefins, polyurethanes, and acid-modified products thereof, and it is particularly preferable to use acid-modified polyolefins and/or polyurethanes.

When the water-insoluble component is acid-modified, the water-insoluble component may be modified with at least one acid anhydride selected from the group consisting of maleic anhydride, succinic anhydride, and phthalic anhydride. A target to be modified with the acid anhydride is preferably polyolefin, more preferably at least one selected from the group consisting of polyethylene, polypropylene, and an ethylene-propylene copolymer, and further preferably an ethylene-propylene copolymer. In addition, the acid anhydride used for modification is preferably maleic anhydride.

Polyurethane is a reaction product of polyol and polyisocyanate. Examples of the polyols include polyether polyols, polyester polyols, polybutadiene polyols, and hydrogenated polybutadiene polyols. Examples of the polyisocyanates include aromatic isocyanates such as diphenylmethane diisocyanate, dimethyldiphenylmethane diisocyanate, tolylene diisocyanate, xylylene diisocyanate, and p-phenylene diisocyanate; alicyclic isocyanates such as dicyclohexylmethane diisocyanate and isophorone diisocyanate; and aliphatic isocyanates such as hexamethylene diisocyanate.

When forming the coating layer on the polymer particle, the polymer particle and a coating material may be mixed to form the coating layer on at least a part of the surface of the polymer particle. The coating material is a component capable of forming the above-mentioned coating layer or a formation material of the component. For example, when the coating layer contains polyurethane, the coating material may contain polyurethane itself, or may contain polyol and polyisocyanate which are formation materials of the polyurethane.

A method of forming the coating layer is not particularly limited. For example, after causing the polymer particles to become in a dispersed state, the coating material can be brought into contact with the polymer particles in the dispersed state to form the coating layer. Specifically, when the coating material is capable of being dissolved in a dispersion medium in which the polymer particles are dispersed, the polymer particles and the coating material may be added to the dispersion medium to form the coating layer on the surfaces of the polymer particles. In addition, when polyol and polyisocyanate are used as the coating material, the polymer particles and polyol are brought into contact with each other by mixing an aqueous solution of polyol with a dispersion liquid of the polymer particles, and thereafter the liquid containing polyisocyanate is mixed to polymerize polyol and polyisocyanate, thereby forming the coating layer containing polyurethane on the surfaces of the polymer particles.

The contact angle of the water-absorbent resin particles can be adjusted by appropriately changing the ratio of the coating material used to form the coating layer. This ratio varies depending on the coating material, but may be 0.01% by mass or more, 0.1% by mass or more, or 0.4% by mass or more, and may be 20% by mass or less, 18% by mass or less, or 16.7% by mass or less, for example. In particular, when the coating layer contains polyurethane, the ratio of the coating material may be 1.5% by mass or less, or 1.3% by mass or less. Furthermore, from the viewpoint of achieving both excellent liquid diffusibility and an excellent amount of re-wet, when the coating layer contains polyurethane, the ratio of the coating material may be 1.0% by mass or less, or 0.9% by mass or less. In these cases, the lower limit value of the ratio of coating material may be the values listed above. The ratio of the coating material is calculated by a method described in Examples to be described later.

The dispersion medium may contain a hydrocarbon solvent. Examples of the hydrocarbon solvent include chain aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene.

[Absorbent Material]

An absorbent material of the present embodiment contains the water-absorbent resin particles of the present embodiment. The absorbent material may contain a fibrous substance, and it is a mixture containing water-absorbent resin particles and the fibrous substance, for example. For example, the structure of the absorbent material may be a structure in which the water-absorbent resin particles and the fibrous substance are uniformly mixed, may be a structure in which the water-absorbent resin particles are sandwiched between the fibrous substances formed in the form of a sheet or a layer, or may be other structures.

Examples of the fibrous substance include finely pulverized wood pulp; cotton; cotton linter; rayon; cellulosic fibers such as cellulose acetate; synthetic fibers such as polyamide, polyester and polyolefin; and a mixture of these fibers. The fibrous substance may be used alone, or may be used in combination of two or more. As the fibrous substance, hydrophilic fibers can be used.

In order to enhance the morphological retention before and during use of the absorbent material, the fibers may be adhered to each other by adding an adhesive binder to the fibrous substance. Examples of the adhesive binder include thermal bonding synthetic fibers, hot melt adhesives, and adhesive emulsions. The adhesive binder may be used alone, or may be used in combination of two or more.

Examples of the thermal bonding synthetic fiber include a total fusion type binder such as polyethylene, polypropylene, and an ethylene-propylene copolymer; and a non-total fusion type binder made of a side-by-side or core-sheath structure of polypropylene and polyethylene. In the above-mentioned non-total fusion type binder, only the polyethylene portion can be thermal-bonded.

Examples of the hot melt adhesive include a mixture of a base polymer such as ethylene-vinyl acetate copolymer, styrene-isoprene-styrene block copolymer, styrene-butadiene-styrene block copolymer, styrene-ethylene-butylene-styrene block copolymer, styrene-ethylene-propylene-styrene block copolymer, and amorphous polypropylene with a tackifier, a plasticizer, an antioxidant, or the like.

Examples of the adhesive emulsion include a polymerization product of at least one monomer selected from the group consisting of methyl methacrylate, styrene, acrylonitrile, 2-ethylhexyl acrylate, butyl acrylate, butadiene, ethylene, and vinyl acetate.

The absorbent material of the present embodiment may contain an inorganic powder (for example, amorphous silica), a deodorant, an antibacterial agent, a dye, a pigment, a fragrance, a sticking agent, or the like. In a case where the water-absorbent resin particles contain inorganic particles, the absorbent material may contain an inorganic powder in addition to the inorganic particles of the water-absorbent resin particles.

The shape of the absorbent material of the present embodiment may be a sheet shape, for example. The thickness of the absorbent material (for example, thickness of the sheet shaped absorbent material) may be 0.1 to 20 mm or 0.3 to 15 mm.

[Absorbent Article]

An absorbent article of the present embodiment includes the absorbent material of the present embodiment. Examples of other constituent members of the absorbent article include a core wrap that retains an absorbent material and prevents falloff or flow of a constituent member of the absorbent material; a liquid permeable sheet disposed on the outermost part at the side where the liquid to be absorbed enters; and a liquid impermeable sheet disposed on the outermost part at the opposite side to the side where the liquid to be absorbed enters. Examples of the absorbent article include diapers (for example, paper diapers), toilet training pants, incontinence pads, sanitary materials (sanitary napkins, tampons, and the like), sweat pads, pet sheets, portal toilet members, and animal excrement treatment materials.

Figure 1:
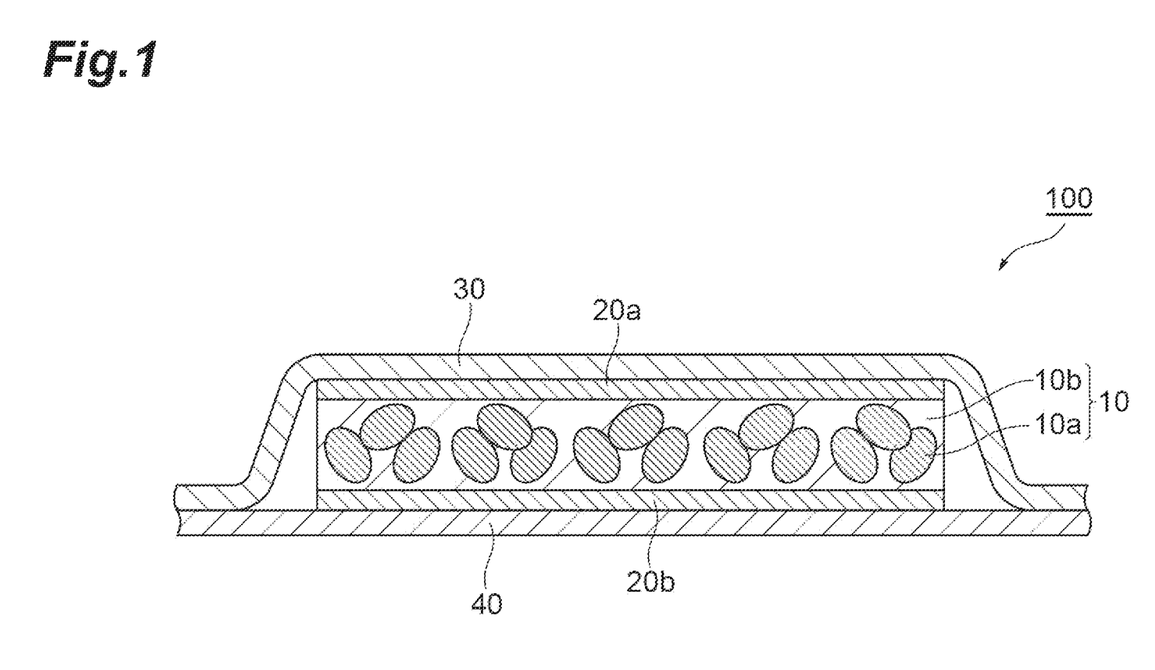
FIG. 1 is a cross-sectional view showing an example of an absorbent article.

FIG. 1 is a cross-sectional view showing an example of an absorbent article. An absorbent article 100 shown in FIG. 1 includes an absorbent material 10, core wrap sheets 20a and 20b, a liquid permeable sheet 30, and a liquid impermeable sheet 40. In the absorbent article 100, the liquid impermeable sheet 40, the core wrap sheet 20b, the absorbent material 10, the core wrap sheet 20a, and the liquid permeable sheet 30 are laminated in this order. In FIG. 1, there is a portion shown so that there is a gap between the members, but the members may be in close contact with each other without the gap.

The absorbent material 10 has water-absorbent resin particles 10a of the present embodiment and a fiber layer 10b containing a fibrous substance. The water-absorbent resin particles 10a are dispersed in the fiber layer 10b.

The core wrap sheet 20a is disposed on one surface side of the absorbent material 10 (the upper side of the absorbent material 10 in FIG. 1) in a state of being in contact with the absorbent material 10. The core wrap sheet 20b is disposed on the other surface side of the absorbent material 10 (the lower side of the absorbent material 10 in FIG. 1) in a state of being in contact with the absorbent material 10. The absorbent material 10 is disposed between the core wrap sheet 20a and the core wrap sheet 20b. Examples of the core wrap sheets 20a and 20b include tissues, non-woven fabrics, woven fabrics, synthetic resin films having liquid permeation holes, and net-like sheets having a mesh. The core wrap sheet 20a and the core wrap sheet 20b each have a main surface having the same size as that of the absorbent material 10, for example.

The liquid permeable sheet 30 is disposed on the outermost part at the side where the liquid to be absorbed enters. The liquid permeable sheet 30 is disposed on the core wrap sheet 20a in a state of being in contact with the core wrap sheet 20a. Examples of the liquid permeable sheet 30 include a non-woven fabric made of a synthetic resin such as polyethylene, polypropylene, polyester, and polyamide, and a porous sheet. The liquid impermeable sheet 40 is disposed on the outermost part at the opposite side to the liquid permeable sheet 30 in the absorbent article 100. The liquid impermeable sheet 40 is disposed below the core wrap sheet 20b in a state of being in contact with the core wrap sheet 20b. Examples of the liquid impermeable sheet 40 include a sheet made of a synthetic resin such as polyethylene, polypropylene, and polyvinyl chloride, and a sheet made of a composite material of these synthetic resins and a non-woven fabric. The liquid permeable sheet 30 and the liquid impermeable sheet 40 have a main surface wider than the main surface of the absorbent material 10, and outer edges of the liquid permeable sheet 30 and the liquid impermeable sheet 40 are present around the absorbent material 10 and the core wrap sheets 20a and 20b.

The magnitude relationship between the absorbent material 10, the core wrap sheets 20a and 20b, the liquid permeable sheet 30, and the liquid impermeable sheet 40 is not particularly limited, and is appropriately adjusted according to the use of the absorbent article or the like. In addition, the method of retaining the shape of the absorbent material 10 using the core wrap sheets 20a and 20b is not particularly limited, and as shown in FIG. 1, the absorbent material may be wrapped by a plurality of core wrap sheets, and the absorbent material is wrapped by one core wrap sheet.

According to the present embodiment, it is possible to provide a liquid absorbing method using the water-absorbent resin particles, the absorbent material or the absorbent article of the present embodiment. The liquid absorbing method of the present embodiment includes a step of bringing the liquid to be absorbed into contact with the water-absorbent resin particles, the absorbent material or the absorbent article of the present embodiment.

EXAMPLES

Hereinafter, the present invention will be more specifically described with reference to examples. However, the present invention is not limited to these examples.

<Polymer Particle>

Production Example 1

(First Stage Polymerization)

A round-bottomed cylindrical separable flask with the inner diameter of 11 cm and the internal volume of 2 L equipped with a reflux cooling device, a dropping funnel, a nitrogen gas introduction tube, and a stirrer (a stirring blade having two stages of four inclined paddle blades with the blade diameter of 5 cm) was prepared. To this separable flask, 293 g of n-heptane, and 0.736 g of a maleic anhydride-modified ethylene-propylene copolymer (Mitsui Chemicals, Inc., Hi-Wax 1105A) as a dispersant were injected and mixed. After dissolving the dispersant in n-heptane by raising the temperature to 80° C. while stirring the mixture in the flask, the mixture was cooled to 50° C.

92.0 g (acrylic acid: 1.03 mol) of an aqueous solution of 80.5% by mass acrylic acid was put in a beaker having the internal volume of 300 mL as a water-soluble ethylenically unsaturated monomer, and while cooling from the outside, 147.7 g of an aqueous solution of 20.9% by mass sodium hydroxide was added dropwise into the beaker to neutralize 75 mol % of acrylic acid. Subsequently, 0.092 g of hydroxyethyl cellulose (Sumitomo Seika Chemicals Co., Ltd., HEC AW-15F) as a thickener, 0.0736 g (0.272 mmol) of potassium persulfate as a radical polymerization initiator, and 0.010 g (0.057 mmol) of ethylene glycol diglycidyl ether as an internal crosslinking agent were added and dissolved to prepare a first stage aqueous solution.

After adding the first stage aqueous solution to the above-mentioned separable flask, stirring was performed for 10 minutes. Subsequently, a surfactant solution in which 0.736 g of sucrose stearic acid ester (Mitsubishi-Chemical Foods Corporation, Ryoto Sugar Ester S-370, HLB: 3), which is a surfactant, was dissolved in 6.62 g of n-heptane was added to the flask to obtain a reaction solution. The inside of the system was sufficiently replaced with nitrogen while stirring the reaction solution at the rotation speed of 550 rpm of the stirrer. Thereafter, the flask was immersed in a water bath at 70° C. to raise the temperature of the reaction solution, and a polymerization reaction was caused to advance for 60 minutes to obtain a first stage polymerization slurry solution.

(Second Stage Polymerization)

128.8 g (acrylic acid: 1.43 mol) of an aqueous solution of 80.5% by mass acrylic acid was put in a beaker having the internal volume of 500 mL, and while cooling from the outside, 159.0 g of an aqueous solution of 27% by mass sodium hydroxide was added dropwise to neutralize 75 mol % of acrylic acid. 0.103 g (0.381 mmol) of potassium persulfate as a radical polymerization initiator and 0.0116 g (0.067 mmol) of ethylene glycol diglycidyl ether as an internal crosslinking agent were added to the beaker containing the aqueous solution of acrylic acid after neutralization, and these were dissolved to prepare a second stage aqueous liquid.

While stirring at the rotation speed of 1000 rpm of the stirrer, the first stage polymerization slurry solution in the above-mentioned flask was cooled to 25° C., and the total amount of the second stage aqueous solution was added. After replacing the inside of the flask with nitrogen for 30 minutes, the flask was immersed in a water bath at 70° C. again to raise the temperature of the reaction solution, and a second stage polymerization reaction was performed for 60 minutes to obtain a hydrogel-like polymer. Thereafter, the above-mentioned flask was immersed in an oil bath set at 125° C., and 257.7 g of water was extracted to the outside of the system by azeotropic distillation of n-heptane and water. Subsequently, the flask was pulled up to make a state in which the lower part thereof was slightly in contact with the oil bath, and the internal temperature was adjusted to 83° C. Thereafter, 4.42 g (0.507 mmol) of an aqueous solution of 2% by mass ethylene glycol diglycidyl ether was added to the flask as a surface crosslinking agent, and the internal temperature of the mixture was maintained at 83° C. for 2 hours.

Thereafter, the flask was immersed in an oil bath again, and n-heptane was removed by drying at 125° C. to obtain a dried product (polymerization product). This dried product was passed through a sieve having the opening of 850 μm to obtain 220.8 g of polymer particles A. The median particle diameter of the polymer particles A was 357 μm.

Production Example 2

220.8 g of polymer particles B was obtained in the same manner as that in Production Example 1, except that, in the hydrogel polymer obtained after the second stage polymerization, 254.4 g of water was extracted to the outside of the system by azeotropic distillation of n-heptane and water. The median particle diameter of the polymer particles B was 364 μm.

Production Example 3

400.0 g (acrylic acid: 4.46 mol) of an aqueous solution of 80.5% by mass acrylic acid was put in a beaker having the internal volume of 2 L as a water-soluble ethylenically unsaturated monomer, and while cooling from the outside, 480.6 g of an aqueous solution of 28.2% by mass sodium hydroxide was added dropwise into the beaker to neutralize 75 mol % of acrylic acid. Subsequently, 0.66 g (2.23 mmol) of trimethylolpropane triacrylate as an internal crosslinking agent and 133.1 g of ion-exchanged water were added and dissolved to prepare a reaction solution.

The reaction solution replaced with nitrogen for 30 minutes was supplied to a reactor formed by attaching a lid to a stainless steel double arm kneader with jacket having the internal volume of 5 L and having two sigma-shaped blades, and the inside the reactor was replaced with nitrogen while maintaining the temperature at 30° C. Subsequently, when 1.47 g (ammonium persulfate: 1.93 mmol) of 30% by mass ammonium persulfate and 1.10 g (L-ascorbic acid: 0.125 mmol) of 2% by mass L-ascorbic acid as a polymerization initiator were added while stirring the reaction solution at the rotation speed of 30 rpm, the polymerization started after about 1 minute. The polymerization reaction was caused at 30° C. for 60 minutes to obtain a hydrogel-like polymer. The hydrogel-like polymer was refined into the diameter of about 5 mm.

The refined hydrogel-like polymer was evenly spread on a fluororesin-coated vat and dried with hot air at 150° C. for 90 minutes to obtain a dried product. The dried product was pulverized using a high-speed pulverizer (ZM-200; manufactured by Retsch). The pulverized powder was passed through a sieve having the opening of 850 μm to obtain an amorphous crushed polymer particle precursor having the average particle diameter of 425 μm.

A surface crosslinking agent solution containing 10 parts by mass of propylene glycol and 0.5 parts by mass of ethylene glycol diglycidyl ether as a surface crosslinking agent, 30 parts by mass of water, and 10 parts by mass of isopropyl alcohol was prepared.

40 g of the polymer resin precursor was injected to a round-bottomed cylindrical separable flask with the inner diameter of 11 cm and the internal volume of 2 L equipped with a Teflon anchoring blade as a stirrer, and while stirring at the rotation speed of 500 rpm, 4.04 g of the surface crosslinking agent solution was added dropwise and mixed for 1 minute. The mixture was dried with hot air at 180° C. for 40 minutes to obtain polymer particles C. The median particle diameter of the polymer particles C was 430 μm.

(Median Particle Diameter)

The particle size distribution of 5 g of the water-absorbent resin particles was measured using an Automated Sonic Sieving Particle Size Analyzer (Robot Sifter RPS-205, manufactured by SEISHIN ENTERPRISE Co., Ltd.), JIS standard sieves having the openings of 850 μm, 710 μm, 600 μm, 500 μm, 400 μm, 300 μm, 250 μm, and 150 μm, and a tray. The relationship between the opening of the sieve and the integrated value of the mass percentage of the particles remaining on the sieve was plotted on a logarithmic probability paper by integrating in the order from the one having the largest particle diameter on the sieve with respect to this particle size distribution. By connecting the plots on the probability paper with a straight line, the particle diameter corresponding to the cumulative mass percentage of 50% by mass was obtained as the median particle diameter.

<Water-Absorbent Resin Particle>

Example 1

A round-bottomed cylindrical separable flask with the inner diameter of 11 cm and the internal volume of 2 L equipped with a reflux cooling device, a dropping funnel, a nitrogen gas introduction tube, and a stirrer (a stirring blade having two stages of four inclined paddle blades with the blade diameter of 5 cm) was prepared. 480 g of n-heptane and 40 g of the polymer particles A were injected to this flask and stirred at 1000 rpm to obtain an n-heptane dispersion liquid of the polymer particles A. A mixture (1) of 1.52 g of distilled water and 0.08 g of a polyether polyol (AGC Inc., EXCENOL 750ED) was added to this dispersion liquid and stirred for 30 minutes, and thereafter a mixture (2) of 0.86 g of acetone and 0.095 g of toluene diisocyanate was further added and stirred for 120 minutes. Subsequently, the flask was immersed in an oil bath set at 125° C., and water was extracted to the outside of the system while refluxing n-heptane by azeotropic distillation of n-heptane and water.

Thereafter, n-heptane was removed by drying at 125° C. to obtain a dried product. The dried product was passed through a sieve having the opening of 850 μm to obtain 36 g of water-absorbent resin particles having the coating layer containing polyurethane.

Example 2

36 g of water-absorbent resin particles was obtained in the same manner as in Example 1 except that the mixture (1) was changed to a mixture of 3.04 g of distilled water and 0.16 g of a polyether polyol (EXCENOL 750ED), and the mixture (2) was changed to a mixture of 1.72 g of acetone and 0.19 g of toluene diisocyanate.

Example 3

36 g of water-absorbent resin particles was obtained in the same manner as in Example 1 except that the mixture (1) was changed to a mixture of 4.56 g of distilled water and 0.24 g of a polyether polyol (EXCENOL 750ED), and the mixture (2) was changed to a mixture of 2.57 g of acetone and 0.29 g of toluene diisocyanate.

Example 4

The same flask as in Example 1 was prepared. 250 g of n-heptane, 100 g of the polymer particles A, and 20 g of a maleic anhydride-modified ethylene-propylene copolymer (Mitsui Chemicals, Inc., Hi-Wax 1105A) were injected into the flask, and while stirring at 1000 rpm, the temperature was raised to 85° C., and the mixture was stirred for 10 minutes.

Thereafter, n-heptane was removed by drying at 125° C. to obtain a dried product. The dried product was passed through a sieve having the opening of 850 μm to obtain 112 g of water-absorbent resin particles having the coating layer containing the maleic anhydride-modified ethylene-propylene copolymer.

Comparative Example 1

The polymer particles A were used as water-absorbent resin particles.

Comparative Example 2

The polymer particles B were used as water-absorbent resin particles.

Comparative Example 3

30 g of the water-absorbent resin particles were collected from a children's diaper "Goo.N Smooth Breathable Pants (Goo.N Massarasara-Tuki-Pants) L Size for Boys" of Daio Paper Corporation. The median particle diameter of the water-absorbent resin particles was 388 μm.

Comparative Example 4

The polymer particles C were used as water-absorbent resin particles.

The water-absorbent resin particles were evaluated as follows. The results are shown in Table 1 and Table 2.

(Ratio of Coating Material)

The ratio of the coating material in the production of the water-absorbent resin particles was calculated by the following formula.

Ratio of coating material (% by mass)={mass of coating material provided to form coating layer/ (mass of polymer particles provided to form coating layer+mass of coating material provided to form coating layer)}×100

(Water Retention Amount)

The water retention amount (at room temperature) of physiological saline of the water-absorbent resin particles was measured by the following procedure. First, a cotton bag (cotton broadcloth No. 60, 100 mm in width×200 mm in length) into which 2.0 g of the water-absorbent resin particles had been weighed was placed in a beaker having the internal volume of 500 mL. After pouring 500 g of physiological saline into the cotton bag containing the water-absorbent resin particles at one time so that lumps could not be produced, the upper part of the cotton bag was bound with a rubber band and the cotton bag was left to stand for 30 minutes to swell the water-absorbent resin particles. The cotton bag after a lapse of 30 minutes was dehydrated for 1 minute using a dehydrator (manufactured by KOKUSAN Co., Ltd., product number: H-122) which had been set to have the centrifugal force of 167 G, and the mass Wa [g] of the cotton bag containing the swollen gel after dehydration was measured. The same operation was performed without addition of the water-absorbent resin particles, the empty mass Wb [g] at the time when the cotton bag was wet was measured, and the physiological saline retention amount of the water-absorbent resin particles was calculated from the following formula.

Water retention amount [g/g]=$(Wa-Wb)/2.0$ (Water Absorption Rate by Vortex Method)

A 100 mL beaker having a rotor (8 mm×30 mm, no ring) was added with 50 g of physiological saline and maintained at 25° C. in a constant-temperature tank. Subsequently, 2.0 g of the water-absorbent resin particles for evaluation were injected into a vortex of the physiological saline stirred at 600 rpm to start measurement with a stopwatch at the same time. The time point when the vortex disappeared and the liquid surface became horizontal was defined as an end point, and the time (seconds) until then was defined as the water absorption rate.

(Liquid Permeability)

The measurement was performed at room temperature. 0.20 g of the water-absorbent resin particles classified into the size of 250 to 500 μm were uniformly put in a plexiglass cylindrical container (1) with the inner diameter of 26 mm, the outer diameter of 40 mm, and the height of 80 mm to which a nylon mesh sheet (250 mesh) was adhered, and a plexiglass cylindrical container (2) with the inner diameter of 19 mm, the outer diameter of 25 mm, and the height of 120 mm to which a similar nylon mesh sheet was adhered from the upper part was inserted to be used as a measurement unit. The mesh side of the measurement unit was immersed in a petri dish with the inner diameter of about 90 mm containing 30 g of physiological saline to cause swelling for 30 minutes, thereby forming a swollen gel.

Subsequently, the entire measurement unit was moved onto an empty petri dish, a 200 g weight was slowly placed on the upper part of the cylindrical container (2), and the swollen gel was loaded for 3 minutes.

A wire mesh with the size of 100 mm×100 mm having a lattice opening of 2 mm square was placed on a petri dish (We) for which the empty mass was measured, and the measurement unit containing the swollen gel was further placed thereon. Subsequently, 20 g of physiological saline was added from the upper part of the cylindrical container (2), and the stopwatch was started at the same time. A mass (Wf) of the petri dish containing the physiological saline that has passed through the swollen gel and flowed out until 30 seconds (0.5 minutes) elapsed from the injection was measured, and the liquid permeation speed (g/min) was calculated by the following formula.

Liquid permeability (g/min)=$(Wf-We)/0.5$ (Contact Angle)

The measurement of the contact angle was performed in the environment of the temperature of 25° C. and the humidity of 50° C.±10%. A double-sided tape (NICETACK manufactured by NICHIBAN Co., Ltd.: 10 mm×75 mm) was attached to a glass slide (25 mm×75 mm) to prepare the glass slide on which an adhesive surface was exposed. First, 1.0 g of the water-absorbent resin particles was uniformly scattered on the double-sided tape attached to the slide. Thereafter, the slide was stood vertically to remove excess water-absorbent resin particles, thereby producing a measurement sample.

A microscope (manufactured by KEYENCE CORPORATION: VHX-5000) consists of a vertically movable sample mounting stage, and a free-angle observation stand having a scope fixing unit that can move up to 90 degrees downward when being parallel to the stage is 0 degrees. The measurement of the contact angle was performed by the following procedure using the above-mentioned microscope, a micropipette (manufactured by GILSON, Pipetman, capacity 100 to 1000 μL), and a pipette tip (Eppendorf ep T.I.P.S. Standard, 50 to 1000 μL).

A scope part of the microscope was adjusted to be horizontal to a stage part, and the measurement sample was placed on the center of the stage part. A tip end part of the pipette tip attached to the micropipette was placed vertically above the surface of the measurement sample at the height of 7±1 mm. One drop (0.01 g) of physiological saline measured with the micropipette was added dropwise onto a position where the surface of the sample was smooth, and a motion picture was taken until this liquid was absorbed to the surface of the measurement sample. An image at the time point of t=0.1 (seconds) after the liquid had landed on the sample surface (this time point being defined as t=0 (seconds)) was taken out, and the angle of the straight line connecting the left and right end points and the vertex on the contact surface between the above-mentioned saline droplet and the double-sided tape surface with respect to the double-sided tape surface was measured using the function of the microscope to define this angle as θ/2. A contact angle θ was obtained by doubling this angle. The measurement was repeated 5 times, and an average value was defined as the contact angle of the water-absorbent resin particles. A method of reading the angle is based on JIS R 3257 (1999) "Testing method of wettability of glass substrate".

<Absorbent Material>

12.0 g of the water-absorbent resin particles and 8 g of crushed pulp (Reiflock manufactured by Leonia) were used and uniformly mixed by air papermaking to produce a sheet shaped absorbent material core having the size of 40 cm×12 cm. Subsequently, an absorbent material in which the content rate of the water-absorbent resin particles was 60% by mass was produced by applying the load of 141 kPa to the entire absorbent material core for 30 seconds and pressing it in a state of sandwiching the upper part and the lower part of the absorbent material core between two sheets of tissue paper having the same size as the absorbent material core and having the basis weight of 16 g/m$^2$.

<Absorbent Article>

The absorbent material was sandwiched by disposing a polyethylene air-through type porous liquid permeable sheet with the basis weight of 22 g/m$^2$ having the same size as the absorbent material on the upper surface of the absorbent material, and disposing a polyethylene liquid impermeable sheet with the same size and the same basis weight on the lower surface of the absorbent material, thereby producing an absorbent article. The following evaluations were performed using the absorbent article. The results are shown in Table 1 and Table 2.

(Preparation of Test Solution)

9866.0 g of distilled water, 100.0 g of sodium chloride, 3.0 g of calcium chloride dihydrate, 6.0 g of magnesium chloride hexahydrate, 25.0 g of a 1% by mass Triton X solution (mixture of Triton X-100 manufactured by FUJIFILM Wako Pure Chemical Corporation and water), and 0.25 g of food blue No. 1 (for coloration) were mixed to prepare a test solution.

(Amount of Re-Wet)

The test of the amount of re-wet was performed in a room adjusted to 25° C. and the humidity of 50% (RH). The absorbent article was placed on a horizontal table. A liquid injection cylinder having an opening with the inner diameter of 3 cm was placed on the central portion of the absorbent article, and 80 mL of the test solution was injected into the cylinder. The cylinder was removed, and the absorbent article was left to stand as it was. After 30 minutes from the completion of the first test solution injection, the same operation was performed using the cylinder at the same position as the first injection. This operation was performed a total of 5 times.

After a lapse of 60 minutes from the completion of the fifth test solution injection, 40 sheets of 10 cm square filter paper of which the mass (Wd (g)) was previously measured were placed near the test solution injection position on the absorbent article, and a weight having the bottom surface of 10 cm×10 cm and the mass of 5 kg was placed thereon. After loading for 5 minutes, the mass (W (g)) of the filter paper was measured, and the increased mass was defined as the amount of re-wet (g).

Amount of re-wet (g)=$W-Wd$ (Diffusibility)

Figure 2:
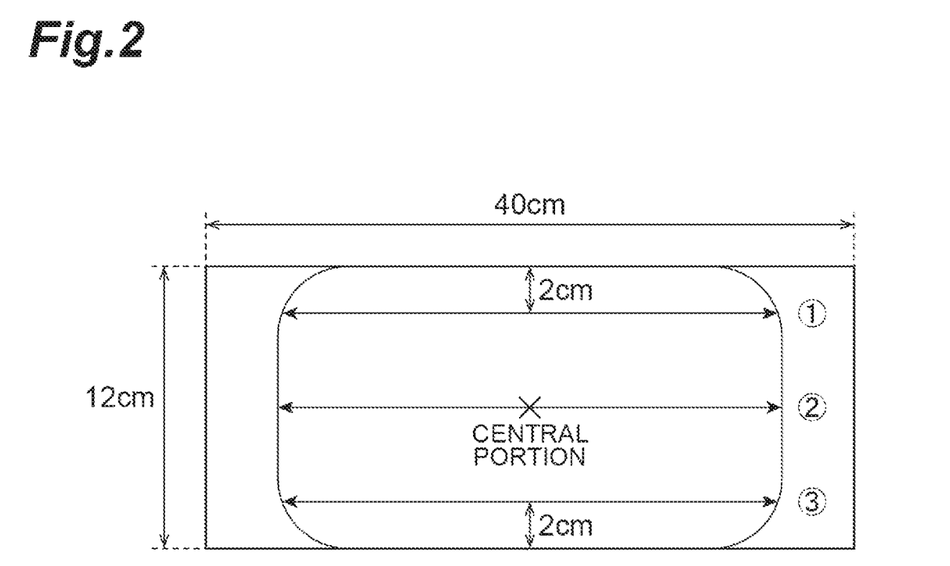
FIG. 2 is an image diagram showing a method of measuring a diffusion distance of a test solution.

After 60 minutes from the completion of the fifth test solution injection, the absorbent material was taken out from the absorbent article, and the length in which the test solution spread was measured. Specifically, as shown in FIG. 2, the diffusion distance of the test solution in a longitudinal direction passing through the central part (a part corresponding to the test solution injection position on the water-absorbent article) of the absorbent material, and the diffusion distance of the test solution in a longitudinal direction passing 2 cm inside from the end of each absorbent material in a lateral direction toward the central part were measured, and an average value of these three values was defined as the diffusion distance (cm).

TABLE 1

| Example | 1 | 2 | 3 | 4 |
|---|---|---|---|---|
| Coating layer | Polyurethane | Polyurethane | Polyurethane | Hi-Wax 1105 A |
| Ratio of coating material (% by mass) | 0.4 | 0.9 | 1.3 | 16.7 |
| Contact angle (degree) | 108 | 114 | 120 | 120 |
| Water absorption rate (sec) | 63 | 68 | 92 | 61 |
| Water retention amount (g/g) | 43 | 40 | 37 | 35 |
| Liquid permeation speed (g/min) | 5 | 10 | 11 | 4 |
| Amount of re-wet (g) | 48 | 48 | 54 | 54 |
| Diffusion distance (cm) | 35 | 35 | 37 | 35 |

TABLE 2

| Comparative Example | 1 | 2 | 3 | 4 |
|---|---|---|---|---|
| Coating layer | — | — | — | — |
| Contact angle (degree) | 87 | 74 | 40 | 51 |
| Water absorption rate (sec) | 38 | 40 | 53 | 100 |
| Water retention amount (g/g) | 40 | 31 | 37 | 33 |
| Liquid permeation speed (g/min) | 4 | 19 | 13 | 16 |
| Amount of re-wet (g) | 46 | 60 | 57 | 59 |
| Diffusion distance (cm) | 31 | 36 | 35 | 38 |

REFERENCE SIGNS LIST

10 . . . absorbent material,
10a . . . water-absorbent resin particle,
10b . . . fiber layer,
20a, 20b . . . core wrap sheet,
30 . . . liquid permeable sheet,
40 . . . liquid impermeable sheet.

The invention claimed is:

1. An absorbent material comprising water-absorbent resin particles, wherein the water-absorbent resin particles comprise a polymer particle having water absorption properties; and a coating layer that coats at least a part of a surface of the polymer particle and contains a water-insoluble component that is at least one selected from the group consisting of polyolefins, polyurethanes, and acid-modified products thereof,
the water-absorbent resin particles have a water absorption rate by a Vortex method of 55 seconds or more,
the water-absorbent resin particles have a water retention amount of physiological saline of 35 g/g to 60 g/g, and
the water-absorbent resin particles have a contact angle with 0.9% by mass saline at 25° C.±2° C. of 100 degrees or larger and 130 degrees or smaller.

2. The absorbent material according to claim 1, wherein the water-absorbent resin particles have a water absorption rate by a Vortex method of 58 seconds or more.

3. The absorbent material according to claim 1, wherein the water-absorbent resin particles have a contact angle with 0.9% by mass saline at 25° C.±2° C. of 120 degrees or smaller and 100 degrees or larger.

4. The absorbent material according to claim 1, wherein the water-absorbent resin particles have a water absorption rate by a Vortex method of 61 seconds or more.

5. The absorbent material according to claim 1, wherein a ratio of a coating material used to form the coating layer is 0.01% by mass to 20% by mass.

6. The absorbent material according to claim 1, wherein the water-absorbent resin particles have a water retention amount of physiological saline of 39 g/g to 45 g/g.

7. The absorbent material according to claim 1, wherein the polyolefins include at least one selected from the group consisting of polyethylene, polypropylene, and an ethylene-propylene copolymer.

8. The absorbent material according to claim 1, wherein the polyurethanes include a reaction product of polyol and polyisocyanate, and the polyisocyanate is aromatic isocyanate.

9. The absorbent material according to claim 1, further comprising a fibrous substance.

10. The absorbent material according to claim 9, wherein the water-absorbent resin particles are mixed with the fibrous substance.

11. The absorbent material according to claim 9, wherein the water-absorbent resin particles define a layer sandwiched by the fibrous substance.

12. The absorbent material according to claim 9, wherein the fibrous substance comprises at least one selected from the group consisting of wood pulp, cotton, cotton linter, rayon, cellulose acetate, polyamide, polyester, and polyolefin.

13. The absorbent material according to claim 9, wherein fibers of the fibrous substance are adhered to each other with an adhesive binder.

14. The absorbent material of claim 9, which is in a form of a sheet having a thickness in the range of 0.1 to 20 mm.

15. An absorbent article comprising the absorbent material of claim 1 and a core wrap surrounding the absorbent material.

16. The absorbent article of claim 15, wherein the core wrap is disposed between a liquid permeable sheet and a liquid impermeable sheet.

* * * * *